US012158461B2

(12) United States Patent
Carbo et al.

(10) Patent No.: US 12,158,461 B2
(45) Date of Patent: Dec. 3, 2024

(54) IDENTIFICATION OF MYCOTOXIN ABSORPTION MATERIALS IN CLAY DEPOSITS

(71) Applicant: Halliburton Energy Services, Inc., Houston, TX (US)

(72) Inventors: Marina Carbo, Powell, WY (US); Thomas S. Cortner, Willis, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 272 days.

(21) Appl. No.: 17/863,278

(22) Filed: Jul. 12, 2022

(65) Prior Publication Data

US 2022/0349868 A1 Nov. 3, 2022

Related U.S. Application Data

(63) Continuation of application No. PCT/US2020/037845, filed on Jun. 16, 2020.

(51) Int. Cl.

*G01N 33/24* (2006.01)
*G01N 23/223* (2006.01)
*G01N 1/28* (2006.01)

(52) U.S. Cl.

CPC ........... *G01N 33/24* (2013.01); *G01N 23/223* (2013.01); *G01N 2001/2866* (2013.01); *G01N 2223/076* (2013.01)

(58) Field of Classification Search

CPC ................. G01N 33/24; G01N 23/223; G01N 2001/2866; G01N 2223/076; G01N 23/20
See application file for complete search history.

(56) References Cited

U.S. PATENT DOCUMENTS

| | | | | |
|---|---|---|---|---|
| 4,495,292 A * | 1/1985 | Siebert | G01N 33/24 73/61.41 |
| 5,556,547 A | 9/1996 | Kajita | |
| 5,741,707 A * | 4/1998 | Herron | G01N 23/20 436/25 |

(Continued)

FOREIGN PATENT DOCUMENTS

WO 2019076820 4/2019

OTHER PUBLICATIONS

E. Vekiru; S. Fruhauf; M. Sahin; F. Ottner; G. Schatzmayr, R. Krska (2007). Investigation of various adsorbents for their ability to bind aflatoxin B1. , 23(1), 27-33.

(Continued)

*Primary Examiner* — David J Bolduc
(74) *Attorney, Agent, or Firm* — Thomas Rooney; C. Tumey Law Group PLLC

(57) ABSTRACT

A method for determining absorption properties in clay deposits is provided that includes obtaining a clay sample, preparing the clay sample, analyzing the clay sample, and applying one or more correlative models to the clay sample. Additionally a system for use in determining absorption properties in clay deposits is provided that includes a plurality of inorganic particles, an analytical instrument configured to gather physical and/or chemical data about the inorganic particles, and a computer system configured to accept the physical and/or chemical data and/or generate correlations between the inorganic particles based on the data.

18 Claims, 4 Drawing Sheets

(56) References Cited

U.S. PATENT DOCUMENTS

| | | | | |
|---|---|---|---|---|
| 10,058,568 | B2 | 8/2018 | Tamames, III | |
| 12,000,853 | B2 * | 6/2024 | Swanson | G01N 21/251 |
| 2004/0013228 | A1 * | 1/2004 | Brotzeller | G01N 23/20<br>378/45 |
| 2016/0339056 | A1 * | 11/2016 | Tamames, III | A61K 33/12 |
| 2018/0202957 | A1 * | 7/2018 | Benoit | G01N 33/241 |
| 2021/0123936 | A1 * | 4/2021 | Swanson | G01N 1/4055 |

OTHER PUBLICATIONS

Deng, Youjun; Liu, Lian; Luisa Barrientos Velazquez, Ana; Dixon, Joe B. (2012). The Determinative Role of the Exchange Cation and Layer-Charge Density of Smectite on Aflatoxin Adsorption. Clays and Clay Minerals, 60(4), 374-386.

D'Ascanio, Vito; Greco, Donato; Menicagli, Elena; Santovito, Elisa; Catucci, Lucia; Logrieco, Antonio F.; Avantaggiato, Giuseppina (2019). The role of geological origin of smectites and of their physico-chemical properties on aflatoxin adsorption. Applied Clay Science, 181( ), 105209-.

International Search Report and Written Opinion for Application No. PCT/US2020/037845, dated Mar. 15, 2021.

Wang, Meichen; Hearon, Sara E.; Phillips, Timothy D. (2019). A high capacity bentonite clay for the sorption of aflatoxins. Food Additives & Contaminants: Part A, ( ), 1-10.

* cited by examiner

IDENTIFICATION OF MYCOTOXIN ABSORPTION MATERIALS IN CLAY DEPOSITS

BACKGROUND

Contamination of animal feed represents an ongoing problem for agricultural, animal raising, and food processing industries. A substantial portion of animal feed supplies, such as grain and hay, become contaminated by mycotoxins produced by invading molds. Mycotoxins are carcinogenic metabolites produced by certain types of fungi and mycotoxin formation may occur when the harmful fungi grow on crops in the field, at harvest, in storage, or during feed processing. One such mycotoxin is aflatoxin, which may be linked to decreased nutritive value and instances of poisoning when present in stored grain or other feeds.

Some varieties of clay minerals may be added to animal feed to reduce the bioavailability of aflatoxins. The bioavailability may be reduced by the binding capabilities of some natural and modified clay minerals to bind to aflatoxin when added to animal feeds to negate or ameliorate the presence of aflatoxins. One clay type that may be useful as an aflatoxin binder are bentonites, which are smectite-rich clays and may be found throughout the world.

Current approaches for testing clay deposits for aflatoxin absorption/binding are time intensive and often costly. One reason for this is that absorption most testing involves collecting clay samples from multiple sources and sending the samples offsite to a wet lab for analysis.

BRIEF DESCRIPTION OF THE DRAWINGS

These drawings illustrate certain aspects of some of the embodiments of the present disclosure and should not be used to limit or define the disclosure.

DETAILED DESCRIPTION

Figure 1:
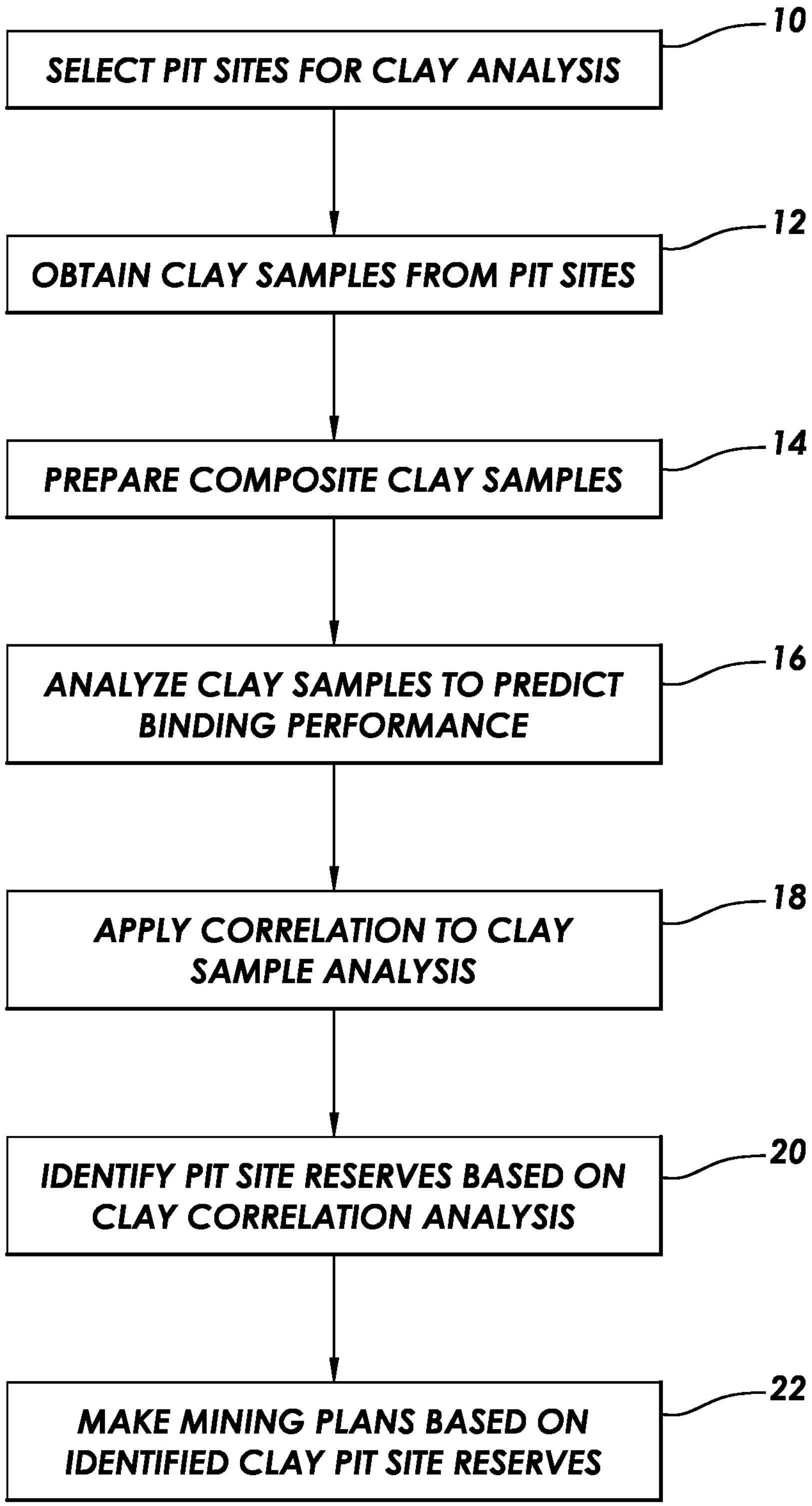
FIG. 1 is a schematic view of a block diagram illustrating a process utilized for identification of an absorbency property in clay deposits according to an embodiment of the present disclosure.

The present disclosure is directed to mycotoxin binders and, in particular, embodiments, may be directed to methods and systems for detection of mycotoxin binders in clay deposit materials from a mine. By way of example, mycotoxin binders, including aflatoxin binders, may be present in clay deposits which is then incorporated and processed as an additive to food stock.

The present disclosure is additionally directed to methods for determining the aflatoxin absorption efficacy of clay deposits, including bentonite, at or near a deposit source. Other aspects of the present disclosure additionally may be used to identify types of bentonite that absorb and bind aflatoxin for use in products. Aspects of the present disclosure may employ multivariate modelling to correlate one or more physical and chemical properties of bentonite and its capacity for binding aflatoxin for the purpose of identifying material in new and existing clay reserves. Additional aspects of the present disclosure may be used to make a determination as to the aflatoxin binding ability of a clay sample and to categorize the clay sample for placement in an alpha pile or a beta pile, where the alpha pile categorization is indicative of a the bentonite sample possessing an aflatoxin binding affinity above a predetermined threshold.

Bentonite is an absorbent aluminum phyllosilicate clay with a composition that includes various amounts of montmorillonite. Varieties of bentonite may be region specific and directly reflect the geologic origin of the source location. Different types of bentonite may be named after the respective dominant element, such as potassium (K), sodium (Na), calcium (Ca), and aluminum (Al). Bentonite is usually formed from the weathering of volcanic ash, often in the presence of water. For industrial purposes, some classes of bentonite include sodium and calcium bentonite. Exemplary bentonite source locations include Montana, other regions of the United States, France, Spain, Greece, Morocco, Italy, Argentina, China, and Turkey.

In some instances, bentonite may be sourced from a mine or pit site. Depending on the location of the mine, including depth of the bentonite deposit, the color of the bentonite clay may be present in a different range of colors. For example, in the Bighorn basin area of Wyoming, the bentonite clay may be in the blue or yellow range. In the Bighorn basin area, yellow bentonite clay deposits tend to lie closer to the surface of the mine, and may have industrial applicability including use in drilling fluids. Additionally, yellow bentonite may include some iron content. Blue bentonite clay deposits may be located less close to the surface of the mine and have lower performance for use in drilling fluids.

The animal feed market is a large volume industry. As such, customers of animal feed mycotoxin binder (bentonite clay) may have high performance expectations for binder additives. Accordingly, accurate identification and characterization of reserves of suitable clay binder additives may be of competitive importance for bentonite clay market suppliers. Current approaches to identifying suitable bentonite clay binder additives may require testing of materials from multiple mining pits for binding performance. Such offsite testing may typically be performed offsite at a third-party laboratory. Such testing may be both time consuming and expensive. Current approaches to performing onsite binding testing have presented a number of challenges. One such challenge is due to the equipment required for aflatoxin binding testing. Another challenge is associated with the health, safety, and environmental challenges associated with working with carcinogenic mycotoxin analytes.

In some embodiments, in accordance with the present disclosure, one or more bulk properties of clay reserves may be analyzed at or near an ongoing mining operation to accurately correlate aflatoxin binding performance. Other aspects of the present disclosure may alleviate one or more drawbacks presented by current testing approaches. It should be noted that while multiple published studies have proposed improvements attempts in testing mycotoxin binding samples, ultimately empirical testing of such studies have been inconclusive and/or have shown relatively low correlation to aflatoxin binding performance. Other current testing approaches, including the ASTM D5890 swell index test, while generally having been acknowledged as a predictor, objective data have shown that swell index tests may show low correlation to mycotoxin binder performance.

Present methods for determining clay aflatoxin absorption have largely relied upon on a free swell index value to identify certain types of desirable materials. One drawback of this approach may be attributed to the fact that the correlation of clay aflatoxin binding performance and free swell value of a given clay sample may not be as reliable as the relationship described by multivariate models disclosed herein. A swell index may also be referred to as free swell index. In soil applications, the free swell index describes when the volume of the soil increases without any application of external forces or water pressure. The index measure indicates the increase in volume with respect to the original volume. For clay applications, free swell index tests are commonly used for identifying expansive clays and to predict the swelling potential.

Development and use of one or more clay analysis models set forth herein may be used to identify certain mycotoxin binding clay reserves for use in feed products in addition to reducing challenges including time intensive testing durations. Additionally, novel models disclosed herein may provide a mycotoxin binding determination using one or more resulting measurements from X-Ray Diffraction (XRD), X-Ray Fluorescence (XRF), and wet lab evaluations rather than absorption isotherms for aflatoxin. Employing one or more of the models in accordance with the present disclosure may decrease the time and expense of qualifying clay reserve materials as an aflatoxin binder, particularly via use of handheld or portable testing equipment whereby XRF or XRD readings may be performed in the field or onsite.

FIG. 1 illustrates a block diagram that may be used to determine one or more attributes indicative of mycotoxin absorption for one or more clay samples according to an aspect of the present disclosure. In block 10, the step of select pit sites for clay analysis is performed. In block 12, the step of obtain clay samples from pit sites is performed. One or more clay samples may be obtained in a variety of ways, including from a clay deposit source, such as a mine. In block 14, the step of prepare composite clay samples is performed. Preparation of composite clay samples may include extraction and preparation of clay samples and further include crushing, drying, and grinding the clay samples. Block 14 may further involve preparation so that the clay sample has a relatively low moisture content (7-8%) and is of a 200-mesh consistency. It will be appreciated that other granularity and mesh values may be used. In block 16, the step of analyze clay samples to predict binding performance is performed. Analysis of the clay samples is performed to determine one or more properties of the clay samples. Clay sample properties may include XRD, XRF, free swell index, PH readings, and determination of clay composition including minerals, metals, and other attributes.

In block 18, the step of applying correlation to clay sample analysis is performed. Block 18 may involve correlating one or more properties of the bentonite/clay samples to known bentonite clays to determine the sample capacity for aflatoxin binding. In general, multivariant modeling techniques as described herein are used to correlate properties with the sample's capacity for aflatoxin binding. Capacity for aflatoxin binding in clay samples may be represented by Qmax. It will be appreciated that Qmax is shown here in units of mol/kg. In some embodiments, multivariant modeling may be used to correlate the one or properties of the bentonite sample to the bentonite sample's Qmax.

In block 20, the step of identify pit site reserves based on clay correlation analysis is performed. Clay sample correlation analysis may include identification of clay deposit locations for later extraction. In block 22, the step of make mining plans based on identified clay pit site reserves is performed.

As described herein, Qmax refers to the absorbency of a particular clay sample. More particularly, the present disclosure sets forth a series of multivariate models in which a predicted Qmax is plotted against actual Qmax values.

Figure 2:
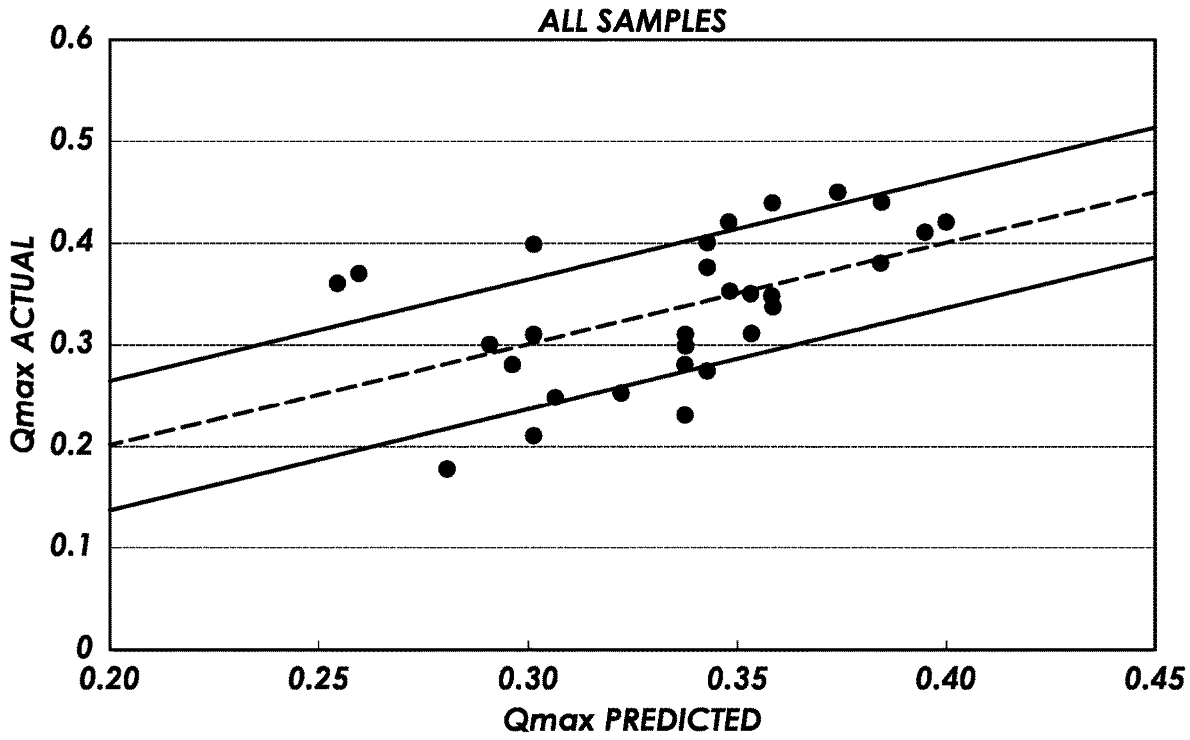
FIG. 2 illustrates a plot of the predictive performance of the free swell index for Qmax versus the actual Qmax values for all bentonite samples according to an embodiment of the present disclosure.

FIG. 2 illustrates a plot of the predictive performance of the free swell index for Qmax versus the actual Qmax values for all of the bentonite samples according to an embodiment of the present disclosure. As shown, the correlation between free swell and Qmax has an R/\2 of 0.2634 and a Root Mean Square Error (RMSE) of 0.0639 versus models which have R/\2 values greater than 0.6 and RMSE values under 0.04. Using free swell alone to predict material with Qmax values greater than or equal to 0.35 would cut off material with a swell index value greater than 16-17, which may eliminate material that performs well and include several samples that do not, as shown in the predictive performance tables set forth herein.

Figure 3:
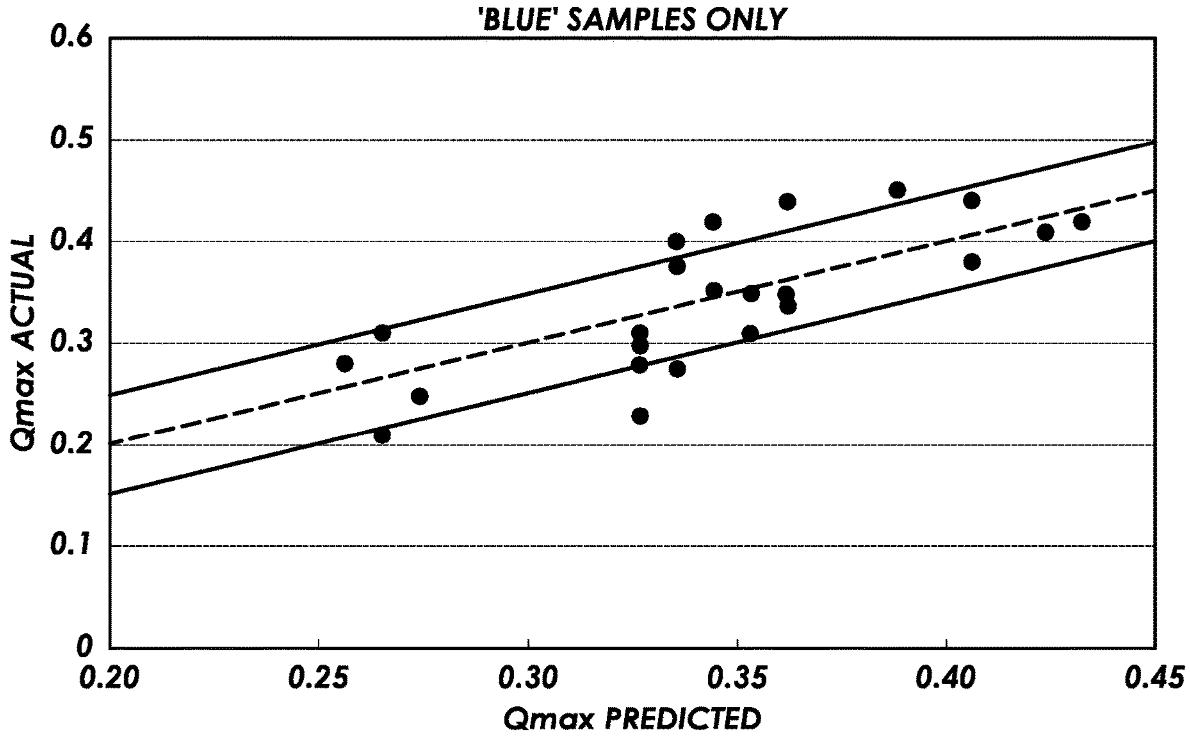
FIG. 3 illustrates a plot of the predictive performance of the free swell index for Qmax versus the actual Qmax values for blue bentonite samples according to an embodiment of the present disclosure.

FIG. 3 illustrates a plot of the predictive performance of the free swell index for Qmax versus the actual Qmax values for the blue bentonite samples according to an embodiment of the present disclosure. As depicted, is a plot whereby the Qmax predicted values are obtained using only the free swell index versus Qmax actual with RMSE bands for all samples tested and for the 'blue' samples. The samples tested originally consisted solely of 'blue' clay samples, and two multivariate models were created using this data. A validation data set was analyzed that included a wider range of samples including some previously untested 'yellow' clay samples. Two multivariate models are used for the full sample set: model #1 which was identified with the 'blue' sample set and model #3 which applies to both sets.

Figure 4:
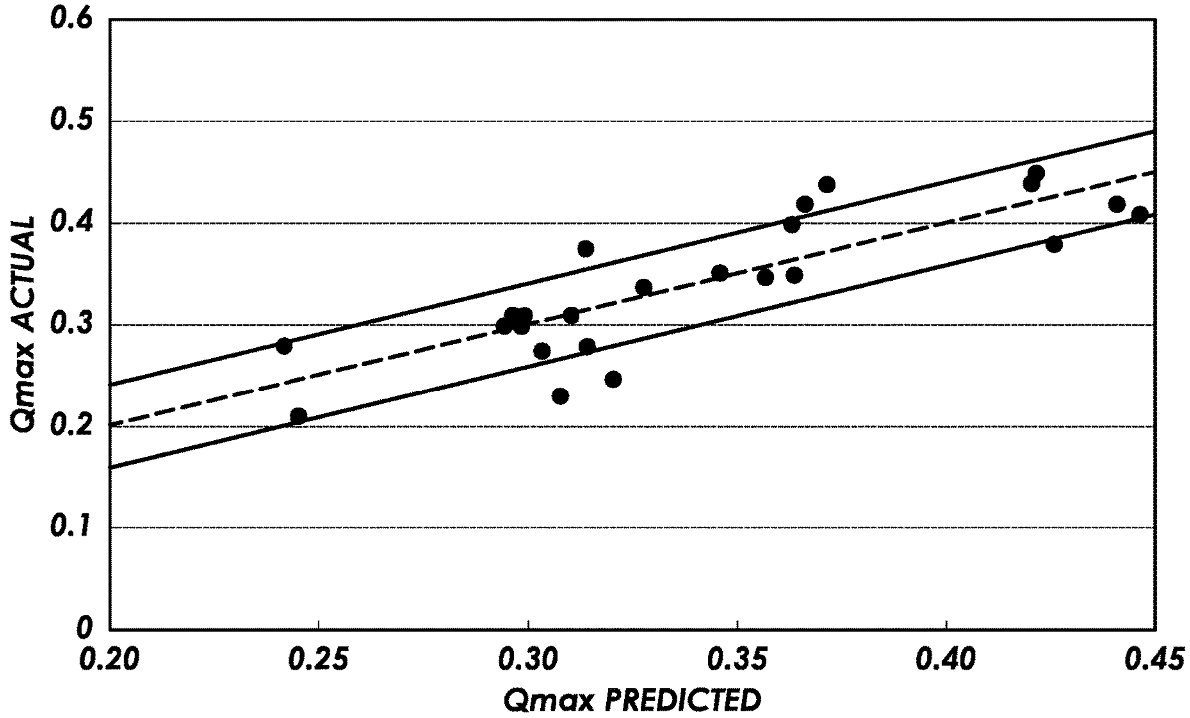
FIG. 4 illustrates a plot of the predictive performance of model #1 for blue bentonite samples according to an embodiment of the present disclosure.

FIG. 4 illustrates a plot of the predictive performance of model #1 for the blue bentonite samples according to an embodiment of the present disclosure. As shown, aflatoxin binding affinities (Qmax) were correlated with results from wet lab, XRD, and XRF testing. Screened physical and chemical properties that showed strong correlations were used in the development of the multivariate models for prediction of aflatoxin binding performance. One of the strongest correlations of Qmax was with the ratio of Magnesium (Mg) to Potassium (K) via XRF analysis. Both models for the 'blue' samples use the free swell and Mg/K and have R/\2 values>0.69. Model #1 uses Mg/K and free swell index. Model #2 uses Mg/K, free swell index, cristobalite, and Fe content. A first exemplary model is as follows:

| Term | Estimate |
|---|---|
| Intercept | 0.3386 |
| Free Swell Index | −0.0064 |
| Wt. % Mg/wt. % K both via XRF | 0.0400 |

$$Q\text{max}=0.3386-(0.0064\times\text{swell})+(0.0400\times Mg/K)$$

Figure 5:
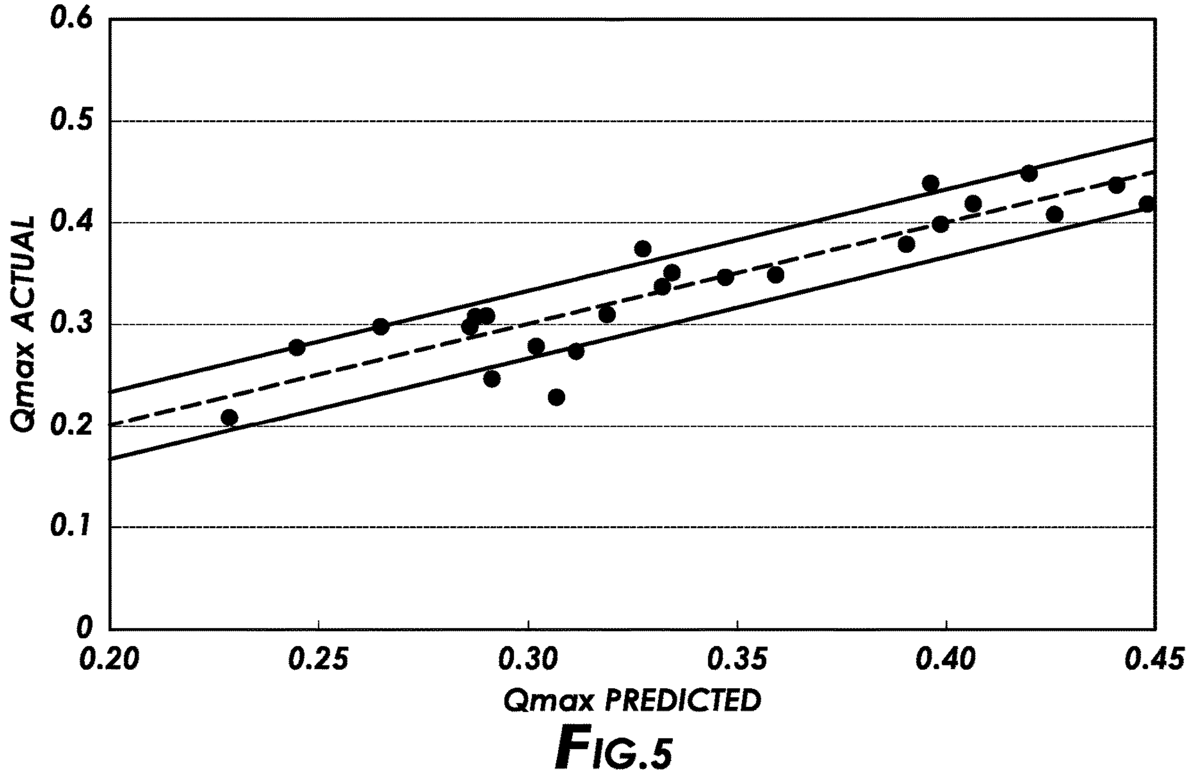
FIG. 5 illustrates a plot of the predictive performance of model #2 with blue bentonite samples according to an embodiment of the present disclosure.

FIG. 5 illustrates a plot of predicted absorbency blue all clay samples using a second model according to an embodiment of the present disclosure, whereby Qmax was predicted with the second model versus Qmax actual with RMSE bands.

Whereby the first model has an $R^2$ of 0.69 and an RMSE of 0.0405, a second exemplary model is as follows:

| Term | Estimate |
| --- | --- |
| Intercept | −0.0573 |
| Wt. % Mg/wt. % K both via XRF | 0.0380 |
| Free Swell Index | −0.0047 |
| Wt. % Fe by XRF | 0.0876 |
| Wt. % Cristobalite by XRD | 0.0137 |

Qmax predicted with Model #2 versus Qmax actual with RMSE bands.

Qmax=−0.0573−(0.0047×swell)+(0.0380×Mg/K)+ (0.0876×Fe)+(0.0137×cristobalite) Model #2 has an $R^2$ of 0.82 and an RMSE of 0.0328.

It will be appreciated that both of the aforementioned exemplary models may show improved predictive performance than using the free swell index alone as a cut off for aflatoxin binder. Turning back to bentonite models, the first model uses free swell index determination and the ratio of magnesium to potassium may be applied to full sample set with an $R^2$ of 0.60 and an RMSE of 0.0482. A third model may use the contents of calcium, barium, and aluminum as well as the product of the weight fraction of magnesium and the smectite content and has an $R^2$ of 0.68 and an RMSE of 0.0412.

An exemplary sample set for the first model is as follows:

| Term | Estimate |
| --- | --- |
| Intercept | 0.3732 |
| Free Swell Index | −0.0072 |
| Wt. % Mg/wt. % K both via XRF | 0.0320 |

Figure 6:
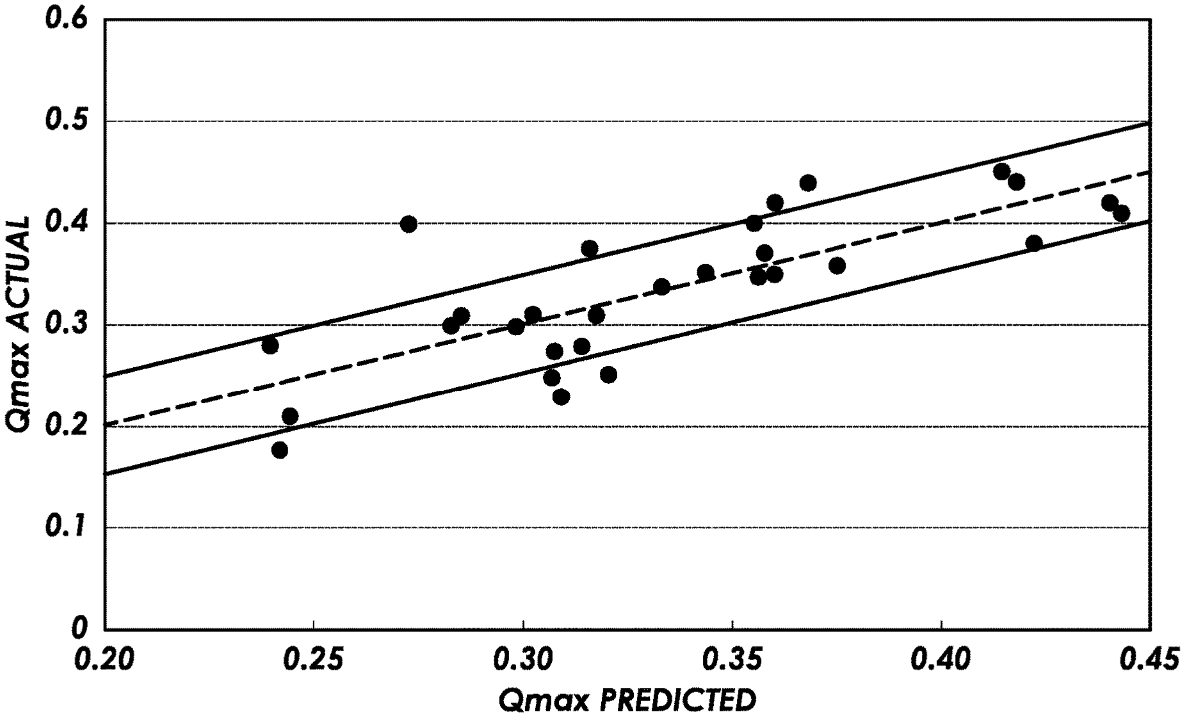
FIG. 6 illustrates a plot of the predictive performance of model #1 with all bentonite samples according to an embodiment of the present disclosure.

FIG. 6 illustrates a plot of predicted absorbency of all clay samples using a first model according to an embodiment of the present disclosure. As shown is Qmax predicted with the first model versus Qmax actual for all samples tested with RMSE bands.

Qmax=0.3732−(0.0072×swell)+(0.0320×Mg/K) Model #1 has an $R^2$ of 0.60 and an RMSE of 0.0482

FIG. 6 illustrates a plot of the predictive performance of model #1 with all of the bentonite samples according to an embodiment of the present disclosure. An exemplary third model set is as follows:

| Term | Estimate |
| --- | --- |
| Intercept | 0.0400 |
| Product of Wt. % smectite by XRD and the wt. fraction of Mg to exchangeable cations all by XRF | 0.0049 |
| Wt. % Ca via XRF | 0.0467 |
| Wt. % Ba via XRF | −0.4059 |
| Wt. % Al via XRF | 0.0091 |

Figure 7:
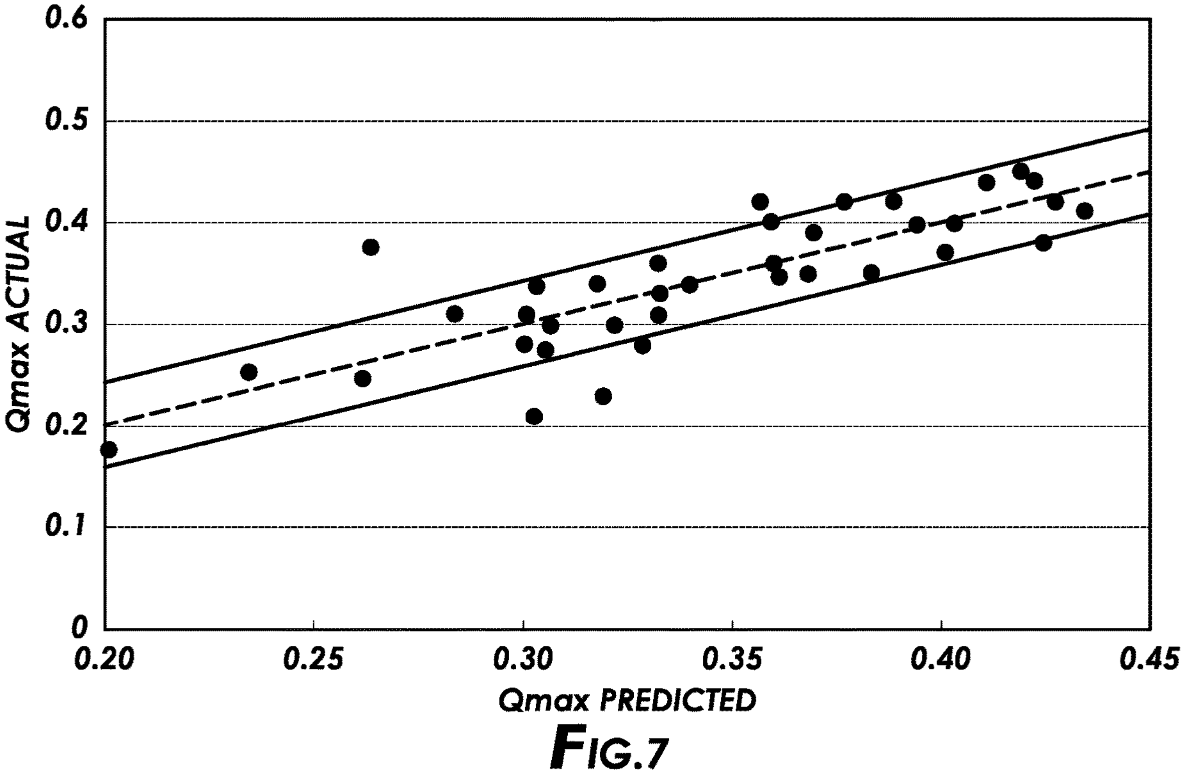
FIG. 7 illustrates a plot of the predictive performance of model #3 with all bentonite samples according to an embodiment of the present disclosure.

FIG. 7 illustrates a plot of the predictive performance of model #3 with all of the bentonite samples according to an embodiment of the present disclosure. As shown, Qmax predicted with third model versus Qmax actual for all samples tested with RMSE bands. Qmax=0.0400+(0.0049× Mg to smectite)+(0.0467×Ca)− (0.4059×Ba)+(0.0091×Al) Model #3 has an $R^2$ of 0.68 and an RMSE of 0.0412.

The multivariate models discussed herein have stronger correlations than the free swell alone. Additionally, validation sets have been performed to quantify model performance. A random subset of samples was removed from the main set and the models were re-made without the subset included. Another model was then used to predict the Qmax values of the removed subset given the analytical data for those samples. The third model predicted the performance of both blue and yellow samples well. However, first and second models performed well for the 'blue' bentonite samples with low fluid performances, whereas predictions for the 'yellow' samples and the high fluid performance 'blue' samples were off by more than 20%. Embodiments in accordance with the instant disclosure, as compared to prior published studies, may indicate improved performance. It will be appreciated that prior approaches, based in part on the selected absorption metric (such as swell index or d-001 spacing) were only able produce moderate correlation, below the performance of one of more of models in this disclosure.

TABLE

Summary of Models

| Model | Clay Type(s) | No. of Data Points | $R^2$ | RMSE |
| --- | --- | --- | --- | --- |
| Only Swell | Blue | 24 | 0.54 | 0.048 |
| Only Swell | All | 29 | 0.26 | 0.064 |
| #1 | Blue | 24 | 0.69 | 0.041 |
| #1 | All | 29 | 0.60 | 0.048 |
| #2 | Blue | 24 | 0.82 | 0.033 |
| #3 | All | 37 | 0.68 | 0.041 |

TABLE

Predictive Performance Plots

| Only Swell with Blue Clays | | Predicted | |
| --- | --- | --- | --- |
| | | ≥0.35 | <0.35 |
| Actual | ≥0.35 | 10 | 2 |
| | <0.35 | 2 | 10 |

| Only Swell with All Clays | | Predicted | |
| --- | --- | --- | --- |
| | | ≥0.35 | <0.35 |
| Actual | ≥0.35 | 10 | 5 |
| | <0.35 | 2 | 12 |

| Model #1 with Blue Clays | | Predicted | |
| --- | --- | --- | --- |
| | | ≥0.35 | <0.35 |
| Actual | ≥0.35 | 11 | 1 |
| | <0.35 | 0 | 12 |

| Model #1 with All Clays | | Predicted | |
| --- | --- | --- | --- |
| | | ≥0.35 | <0.35 |
| Actual | ≥0.35 | 12 | 3 |
| | <0.35 | 0 | 14 |

| Model #2 with Blue Clays | | Predicted | |
| --- | --- | --- | --- |
| | | ≥0.35 | <0.35 |
| Actual | ≥0.35 | 10 | 2 |
| | <0.35 | 0 | 12 |

TABLE-continued

| Predictive Performance Plots | | | |
|---|---|---|---|
| Model #3 with | | Predicted | |
| All Clays | | ≥0.35 | <0.35 |
| Actual | ≥0.35 | 18 | 2 |
| | <0.35 | 0 | 17 |

Additionally, individual correlations of the cations (Na, Ca, K, and Mg) may be used to screen samples for capacity to bind aflatoxin. From the analytical data gathered, aflatoxin binding may favor higher magnesium and calcium levels and lower levels of potassium and sodium. The percent by weight of illite in the samples may also be used as a screen, with samples that are <1% by weight illite favored for aflatoxin binding. Layer spacing may also reflect the trend of increased binding with increased calcium in the bentonite samples tested; samples that are predominantly calcium based on their d-001 layer spacing have higher Qmax values than mixed sodium calcium and predominantly sodium samples.

The preceding description provides various examples of the systems and methods of use disclosed herein which may contain different method steps and alternative combinations of components.

Statement 1. A method for determining absorption properties in clay deposits comprising: obtaining a clay sample, preparing the clay sample, analyzing the clay sample, and applying one or more correlative models to the clay sample.

Statement 2. The method of statement 1 wherein the step of preparing the clay sample includes drying the clay sample.

Statement 3. The method of any preceding statement wherein the step of preparing the clay sample includes crushing the clay sample.

Statement 4. The method of any preceding statement wherein the step of analyzing the clay sample includes performing X-Ray diffraction.

Statement 5. The method of any preceding statement wherein the step of analyzing the clay sample includes performing X-Ray fluorescence.

Statement 6. The method of any preceding statement wherein the step of analyzing the clay sample includes performing X-Ray fluorescence and determining a free swell value.

Statement 7. The method of statement 6 further including performing X-Ray diffraction.

Statement 8. A method of determining absorption properties in clay deposits comprising: obtaining a clay sample, preparing the clay sample, analyzing the clay sample, applying one or more correlative models to the clay sample, and determining the mycotoxin binding performance of the clay sample.

Statement 9. The method of statement 8 further comprising the step of categorizing the clay sample into an alpha pile or a beta pile.

Statement 10. The method of statement 8 or statement 9 wherein the step of preparing the clay sample includes crushing the clay sample.

Statement 11. The method of any one of statements 8 to 10 wherein the step of analyzing the clay sample includes performing X-Ray fluorescence and determining a free swell value.

Statement 12. The method of any one of statements 8 to 11 wherein the step of analyzing the clay sample includes performing X-Ray fluorescence.

Statement 13. The method any one of statements 8 to 12 wherein the step of analyzing the clay sample includes performing X-Ray diffraction and determining a free swell value.

Statement 14. A system for use in determining absorption properties in clay deposits: a plurality of inorganic particles; an analytical instrument configured to gather physical and/or chemical data about the inorganic particles; and a computer system configured to accept the physical and/or chemical data and/or generate correlations between the inorganic particles based on the data.

Statement 15. The system of statement 14 wherein at least one of the inorganic particles comprises bentonite.

Statement 16. The system of any one of statements 14 to 15 wherein the analytical instrument is configured to perform X-Ray fluorescence.

Statement 17. The system of any one of statements 14 to 16 wherein the analytical instrument is configured to perform X-Ray fluorescence and determine a free swell value.

Statement 18. The system of any one of statements 14 to 17 wherein the analytical instrument is configured to perform X-Ray diffraction.

Statement 19. The system of any one of statements 14 to 18 wherein the analytical instrument is configured to perform X-Ray diffraction and determine a free swell value.

Statement 20. The system of any one of statements 14 to 19 wherein the analytical instrument is configured to perform X-Ray fluorescence, X-Ray diffraction, and determine a free swell value.

It should be understood that, although individual examples may be discussed herein, the present disclosure covers all combinations of the disclosed examples, including, without limitation, the different component combinations, method step combinations, and properties of the system. It should be understood that the compositions and methods are described in terms of "comprising," "containing," or "including" various components or steps, the compositions and methods may also "consist essentially of" or "consist of" the various components and steps. Moreover, the indefinite articles "a" or "an," as used in the claims, are defined herein to mean one or more than one of the element that it introduces. The term "coupled" means directly or indirectly connected.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present examples are well adapted to attain the ends and advantages mentioned as well as those that are inherent therein. The particular examples disclosed above are illustrative only and may be modified and practiced in different but equivalent manners apparent to those skilled in the art having the benefit of the teachings herein. Although individual examples are discussed, the disclosure covers all combinations of all of the examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of those examples. If there is any conflict in the usages of a word or term in this specification and one or more patent(s) or other documents that may be incorporated herein by reference, the definitions that are consistent with this specification should be adopted.

What is claimed is:

1. A method for determining absorption properties in clay deposits comprising:
- obtaining a clay sample;
- preparing the clay sample by at least one of crushing drying or grinding;
- analyzing the clay sample by at least two of X-Ray Diffraction, X-Ray Fluorescence determining a free swell index, PH reading, or determination of clay composition to generate clay sample data; and
- calculating a capacity for aflatoxin binding (Omax) of the clay sample using the clay sample data as an input to one or more multivariant correlative models for determining Qmax.

2. A method of determining absorption properties in clay deposits comprising:
- obtaining a clay sample;
- preparing the clay sample by at least one of crushing drying or grinding;
- analyzing the clay sample by at least two of X-Ray Diffraction, X-Ray Fluorescence determining a free swell index PH reading or determination of clay composition to generate clay sample data;
- applying one or more correlative models to the clay sample data; and
- determining mycotoxin binding performance of the clay sample using the one or more correlative models.

3. The method of claim 2 further comprising the step of categorizing the clay sample into an alpha pile or a beta pile.

4. A system for use in determining absorption properties in clay deposits:
- a plurality of clay sample particles;
- an analytical instrument configured to gather physical and/or chemical data about the inorganic particles; and
- a computer system configured to accept the physical and/or chemical data and/or generate correlations between the inorganic particles based on the data and calculate a capacity for aflatoxin binding (Omax) of the clay sample using the physical and/or chemical data as an input to one or more multivariant correlative models for determining Qmax.

5. The system of claim 4 wherein at least one of the inorganic particles comprises bentonite.

6. The system of claim 4 wherein the analytical instrument is configured to perform X-Ray fluorescence.

7. The system of claim 4 wherein the analytical instrument is configured to perform X-Ray fluorescence and determine a free swell value.

8. The system of claim 4 wherein the analytical instrument is configured to perform X-Ray diffraction.

9. The system of claim 4 wherein the analytical instrument is configured to perform X-Ray diffraction and determine a free swell value.

10. The system of claim 4 wherein the analytical instrument is configured to perform X-Ray fluorescence, X-Ray diffraction, and determine a free swell value.

11. The method of claim 1 wherein the one or more multivariant correlative models comprises a correlation of Qmax to a ratio of Mg/K of the clay sample.

12. The method of claim 1 wherein the one or more multivariant correlative models comprises a correlation of Qmax to a ratio of Mg/K of the clay sample and free swell index of the clay sample.

13. The method of claim 1 wherein the one or more multivariant correlative models comprises a correlation of Qmax to a ratio of Mg/K of the clay sample, free swell index of the clay sample, cristobalite content of the clay sample, and iron content of the clay sample.

14. The method of claim 1 wherein the one or more multivariant correlative models comprises a correlation of Qmax to a ratio of Mg/smectite of the clay sample, calcium content of the clay sample, Barium content of the clay sample, and aluminum content of the clay sample.

15. The method of claim 2 wherein the one or more multivariant correlative models comprises a correlation of mycotoxin binding performance to a ratio of Mg/K of the clay sample.

16. The method of claim 2 wherein the one or more multivariant correlative models comprises a correlation of mycotoxin binding performance to a ratio of Mg/K of the clay sample and free swell index of the clay sample.

17. The method of claim 2 wherein the one or more multivariant correlative models comprises a correlation of mycotoxin binding performance to a ratio of Mg/K of the clay sample, free swell index of the clay sample, cristobalite content of the clay sample, and iron content of the clay sample.

18. The method of claim 2 wherein the one or more multivariant correlative models comprises a correlation of mycotoxin binding performance to a ratio of Mg/smectite of the clay sample, calcium content of the clay sample, Barium content of the clay sample, and aluminum content of the clay sample.

* * * * *